(12) United States Patent
Freudiger

(10) Patent No.: US 8,870,925 B2
(45) Date of Patent: Oct. 28, 2014

(54) DYNAMIC CLAMPING DEVICE FOR SPINAL IMPLANT

(75) Inventor: Stefan Freudiger, Bremgarten (CH)

(73) Assignee: Bird Biedermann AG, Sachseln (CH)

( * ) Notice: Subject to any disclaimer, the term of this patent is extended or adjusted under 35 U.S.C. 154(b) by 478 days.

(21) Appl. No.: 11/520,286

(22) Filed: Sep. 12, 2006

(65) Prior Publication Data

US 2007/0093821 A1  Apr. 26, 2007

Related U.S. Application Data

(60) Provisional application No. 60/738,759, filed on Nov. 21, 2005.

(30) Foreign Application Priority Data

Sep. 13, 2005  (CH) ..................................... 01488/05

(51) Int. Cl.
*A61B 17/70* (2006.01)

(52) U.S. Cl.
CPC ......... *A61B 17/7032* (2013.01); *A61B 17/7031* (2013.01)
USPC ....................................... 606/264

(58) Field of Classification Search
USPC ......... 606/245, 254, 264, 265, 267, 246, 257, 606/255, 268, 269, 270, 60, 250–253, 256, 606/258–263, 266, 271–279
See application file for complete search history.

(56) References Cited

U.S. PATENT DOCUMENTS

| | | | | |
|---|---|---|---|---|
| 4,569,338 A | * | 2/1986 | Edwards | 606/278 |
| 4,887,596 A | * | 12/1989 | Sherman | 606/305 |
| 4,987,892 A | | 1/1991 | Krag et al. | |
| 5,190,543 A | * | 3/1993 | Schlapfer | 606/256 |
| 5,261,912 A | * | 11/1993 | Frigg | 606/302 |
| 5,330,473 A | | 7/1994 | Howland | |
| 5,360,431 A | | 11/1994 | Puno et al. | |
| 5,385,583 A | * | 1/1995 | Cotrel | 606/270 |
| 5,474,555 A | * | 12/1995 | Puno et al. | 606/266 |
| 5,520,689 A | * | 5/1996 | Schlapfer et al. | 606/270 |
| 5,536,268 A | * | 7/1996 | Griss | 606/254 |
| 5,716,356 A | * | 2/1998 | Biedermann et al. | 606/271 |
| 5,733,286 A | | 3/1998 | Errico et al. | |

(Continued)

FOREIGN PATENT DOCUMENTS

| | | |
|---|---|---|
| CN | 2534985 Y | 2/2008 |
| EP | 0 669 109 B1 | 8/1995 |

(Continued)

OTHER PUBLICATIONS

International Search Report for Swiss Application No. 01488/05 dated May 30, 2006 and mailed Jun. 19, 2006, 3 pp.

(Continued)

*Primary Examiner* — Jerry Cumberledge
(74) *Attorney, Agent, or Firm* — Christie, Parker & Hale, LLP

(57) ABSTRACT

A Spinal column implant for elastic stabilization of vertebrae includes an elastic rod that is anchored in a non-positive fit fashion in the receptacle of a pedicle screws by means of a mobile filling piece and a clamping element. The non-positive fit is supported additionally by a dynamic form-fit contribution upon exposure to load.

26 Claims, 5 Drawing Sheets

(56) References Cited

U.S. PATENT DOCUMENTS

| | | | |
|---|---|---|---|
| 5,738,685 A * | 4/1998 | Halm et al. | 606/270 |
| 5,928,233 A * | 7/1999 | Apfelbaum et al. | 606/261 |
| 6,077,262 A | 6/2000 | Schläpfer et al. | |
| 6,117,137 A | 9/2000 | Halm et al. | |
| 6,224,598 B1 | 5/2001 | Jackson | |
| 6,302,410 B1 | 10/2001 | Wentworth et al. | |
| 6,443,953 B1* | 9/2002 | Perra et al. | 606/270 |
| 6,478,797 B1* | 11/2002 | Paul | 606/305 |
| 6,540,748 B2 | 4/2003 | Lombardo | |
| 6,540,749 B2* | 4/2003 | Schafer et al. | 606/270 |
| 6,565,565 B1* | 5/2003 | Yuan et al. | 606/272 |
| 6,585,737 B1* | 7/2003 | Baccelli et al. | 606/278 |
| 6,652,526 B1 | 11/2003 | Arafiles | |
| 6,676,661 B1 | 1/2004 | Benlloch et al. | |
| 6,695,843 B2* | 2/2004 | Biedermann et al. | 606/271 |
| 6,783,527 B2* | 8/2004 | Drewry et al. | 606/254 |
| 6,793,657 B2* | 9/2004 | Lee et al. | 606/269 |
| 6,896,677 B1* | 5/2005 | Lin | 606/266 |
| 7,144,396 B2 | 12/2006 | Shluzas | |
| 7,731,749 B2 | 6/2010 | Biedermann et al. | |
| 7,828,825 B2 | 11/2010 | Bruneau et al. | |
| 8,157,843 B2 | 4/2012 | Biedermann et al. | |
| 8,282,672 B2 | 10/2012 | Freudiger | |
| 8,568,458 B2 | 10/2013 | Matthis et al. | |
| 2002/0035366 A1* | 3/2002 | Walder et al. | 606/61 |
| 2003/0083657 A1* | 5/2003 | Drewry et al. | 606/61 |
| 2003/0125741 A1* | 7/2003 | Biedermann et al. | 606/61 |
| 2003/0167058 A1* | 9/2003 | Shluzas | 606/61 |
| 2003/0220642 A1* | 11/2003 | Freudiger | 606/61 |
| 2003/0220643 A1 | 11/2003 | Ferree | |
| 2004/0122425 A1 | 6/2004 | Suzuki et al. | |
| 2004/0138660 A1* | 7/2004 | Serhan | 606/61 |
| 2004/0153068 A1* | 8/2004 | Janowski et al. | 606/61 |
| 2004/0172025 A1 | 9/2004 | Drewry et al. | |
| 2004/0260283 A1* | 12/2004 | Wu et al. | 606/61 |
| 2005/0096659 A1 | 5/2005 | Freudiger | |
| 2005/0131410 A1* | 6/2005 | Lin | 606/61 |
| 2005/0177157 A1* | 8/2005 | Jahng | 606/61 |
| 2005/0203518 A1 | 9/2005 | Biedermann et al. | |
| 2006/0129147 A1 | 6/2006 | Biedermann et al. | |
| 2006/0149233 A1* | 7/2006 | Richelsoph | 606/61 |
| 2006/0271046 A1 | 11/2006 | Kwak et al. | |
| 2007/0093820 A1 | 4/2007 | Freudiger | |
| 2008/0114404 A1 | 5/2008 | Matthis et al. | |
| 2010/0286731 A1 | 11/2010 | Biedermann et al. | |

FOREIGN PATENT DOCUMENTS

| | | | |
|---|---|---|---|
| FR | 2 853 522 | 10/2004 | |
| FR | 2 863 860 | 6/2005 | |
| JP | 2004-97705 A | 4/2004 | |
| WO | WO 97/43974 A1 | 11/1997 | |
| WO | WO 9944527 A1 * | 9/1999 | A61B 17/70 |
| WO | WO 01/06939 A1 | 2/2001 | |
| WO | WO 03024343 A1 * | 3/2003 | A61B 17/70 |
| WO | WO 03043511 A1 * | 5/2003 | A61B 17/70 |
| WO | WO 2005/058173 A1 | 6/2005 | |

OTHER PUBLICATIONS

English translation of JPO Office Action dated May 24, 2011 for counterpart JP Patent Application No. 244264/2006, 5 sheets.
Current claims for U.S. Appl. No. 11/512,461 (6 sheets).
OA dated Oct. 1, 2008 for U.S. Appl. No. 11/512,461 (8 sheets).
OA dated May 22, 2009 for U.S. Appl. No. 11/512,461 (8 sheets).
OA dated Jan. 20, 2010 for U.S. Appl. No. 11/512,461 (9 sheets).
OA dated Aug. 2, 2010 for U.S. Appl. No. 11/512,461 (10 sheets).
OA dated Dec. 17, 2010 for U.S. Appl. No. 11/512,461 (2 sheets).
OA dated Jun. 21, 2011 for U.S. Appl. No. 11/512,461 (7 sheets).
Current claims for U.S. Appl. No. 12/789,162 (3 sheets).
OA dated May 11, 2011 for U.S. Appl. No. 12/789,162 (9 sheets).
OA dated Jan. 4, 2012 for U.S. Appl. No. 12/789,162 (9 sheets).
OA dated Mar. 24, 2009 for U.S. Appl. No. 11/642,566 (7 sheets).
OA dated Oct. 23, 2009 for U.S. Appl. No. 11/642,566 (10 sheets).
OA dated Jun. 10, 2011 for U.S. Appl. No. 11/642,566 (10 sheets).
Current claims for U.S. Appl. No. 11/854,508 (5 sheets).
OA dated Nov. 27, 2009 for U.S. Appl. No. 11/854,508 (13 sheets).
OA dated May 21, 2010 for U.S. Appl. No. 11/854,508 (15 sheets).
OA dated Dec. 7, 2010 for U.S. Appl. No. 11/854,508 (16 sheets).
OA dated May 25, 2011 for U.S. Appl. No. 11/854,508 (3 sheets).
OA dated Jan. 17, 2012 for U.S. Appl. No. 11/854,508 (13 sheets).
OA dated Jan. 23, 2009 for U.S. Appl. No. 11/599,676 (21 sheets).
OA dated Jun. 1, 2012 for U.S. Appl. No. 11/854,508 (12 sheets).
OA dated Nov. 22, 2013 for U.S. Appl. No. 12/488,458 (10 sheets).
OA dated Oct. 11, 2011 for U.S. Appl. No. 12/488,458 (9 sheets).
OA dated Mar. 13, 2014 for U.S. Appl. No, 12/789,162 (6 sheets).
OA dated Aug. 13, 2013 for U.S. Appl. No. 12/789,162 (12 sheets).
OA dated Nov. 9, 2012 for U.S. Appl. No. 13/425,153 (10 sheets).
OA dated Apr. 25, 2013 for U.S. Appl. No. 13/596,888 (7 sheets).
OA dated Feb. 21, 2014 for U.S. Appl. No. 13/596,888 (9 sheets).
OA dated Oct. 2, 2013 for U.S. Appl. No. 13/613,739 (11 sheets).
OA dated Feb. 14, 2014 for U.S. Appl. No. 13/891,141 (12 sheets).

* cited by examiner

DYNAMIC CLAMPING DEVICE FOR SPINAL IMPLANT

CROSS-REFERENCE TO RELATED APPLICATION(S)

The present disclosure claims the benefit of U.S. Provisional Patent Application Ser. No. 60/738,759, filed Nov. 21, 2005, and claims priority from Swiss Patent Application 01488/05, filed Sep. 13, 2005, the entire disclosures of which are incorporated herein by reference.

BACKGROUND

The present disclosure relates to a dynamic stabilizing system for spinal columns capable of stabilizing the spinal column without spinal fusion using elastic connection elements connected to bone or pedicle screws.

A multitude of rod/screw connections are available for metallic rods and used mainly in fusion operations (spinal fusion). There are only a few elastic systems that only support and stabilize, but do not fuse, the spinal segments and, thus, there are only a few devices for attaching the elastic connection elements with the pedicle screws.

As a matter of principle, rod/screw connections that are suitable for metallic rods are not necessarily also suitable for elastic connection elements since elastic rods made of plastic material, for example, possess different properties than rods made of metal that are stiffer by comparison. Accordingly, elastic rods made of plastic material cannot be simply clamped in a permanent fashion by means of non-positive fitting (force-fit, frictional-fit or press-fit) since they usually are capable of reducing the clamping force by flowing. Consequently, there is a need for connection concepts comprising, aside from a possible non-positive fit-type (basic) clamping, a contribution by positive fitting or, ideally, a dynamic positive fit that increases transiently with increasing load and lessens with decreasing load.

WO 01/06939, WO 97/43974 and U.S. Pat. No. 4,987,892 include rotatable holding elements these serve the sole purpose of also connecting rods, which do not extend perpendicular to the screw axis, to the screw. Accordingly, these holding elements are rotatable during the attachment phase only and can no longer be moved after completion of the attachment phase.

SUMMARY OF THE INVENTION

The present disclosure is based on the tasks to connect an elastic rod made of plastic material with a continuous smooth surface in discontinuity-free and secure fashion to a bone or pedicle screw and, in the process, transfer tensile and compressive as well as shearing and torsional forces between neighboring vertebrae.

The solution to this task is characterized in that the connection is a combination of permanent (basic) non-positive fit and a dynamic form-fit contribution. The dynamic form-fit contribution is attained by local elastic or plastic deformation of the plastic rod. This dynamic form-fit contribution increases automatically with increasing axial force in the rod and decreases automatically thereafter with decreasing axial force in the rod.

Accordingly, the non-positive fit rod/screw connection with a dynamic form-fit contribution allows a smooth elastic rod made of plastic material to be connected to the head of a bone or pedicle screw such that the expected forces can be transferred permanently and securely due to its application as a dynamic stabilization of the lumbar spinal column. Thus, a non-positive fit connection, which can be positioned easily and continuously, is combined with the reliability of a form-fit contribution to the connection. In the process, the initial positive-fit is supported by a dynamic increase in the form-fit with increasing axial force, which decreases again with decreasing axial force. This takes care of the plastic rod and largely prevents the process of flowing under load.

BRIEF DESCRIPTION OF THE DRAWINGS

In the following, the present disclosure is illustrated in more detail by means of the appended drawings, in which exemplary embodiments are shown. In the figures, the following is shown schematically.

DETAILED DESCRIPTION OF THE INVENTION

Figure 1A:
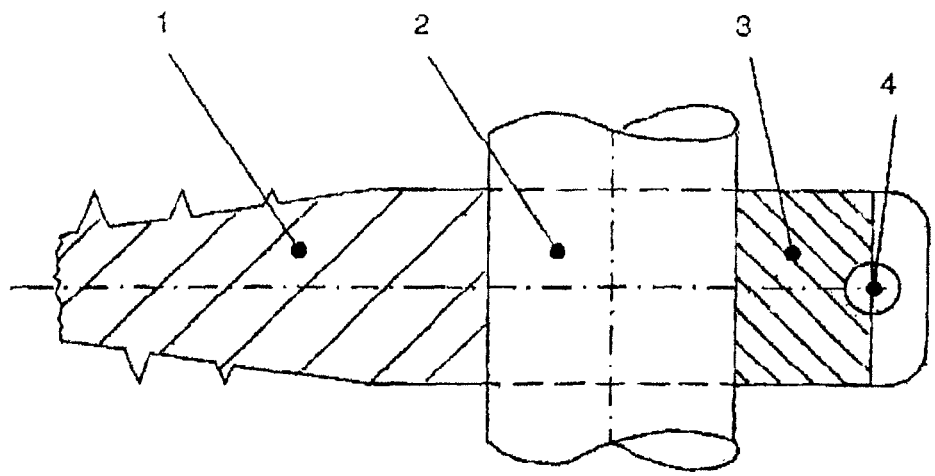
FIG. 1*a* shows an elastic connection element in a (sectioned) pedicle screw with a filling piece in neutral position about a pivot point.
Figure 1B:
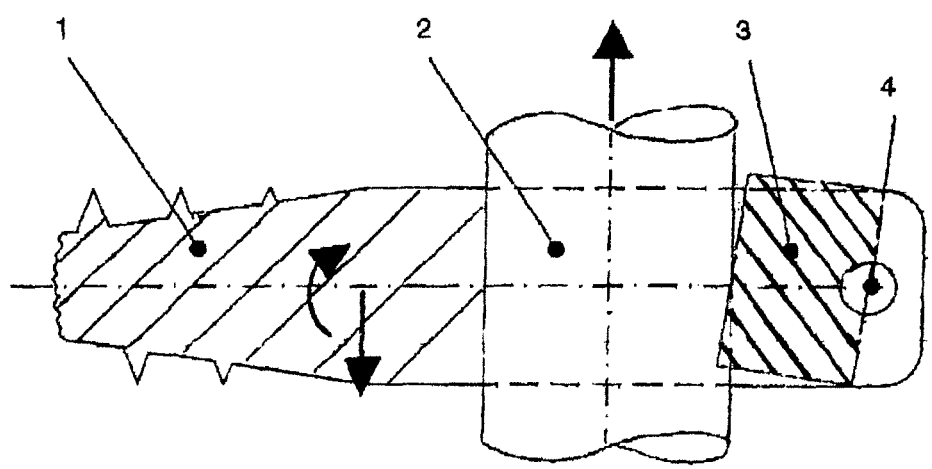
FIG. 1*b* shows an elastic connection element exposed to tensile force with a filling piece in rotated position about a pivot point.

FIG. 1*a* shows a connection element (2) in a pedicle screw (1) (shown in cross section) with a rotatable filling piece (3) in a neutral position about a pivot point (4). The connection element (2) may be a rod of any shape. For example, the connection element can have a round cross-sectional shape. The connection element (2) is elastic and is constructed from a plastic material. An example of such a material is Polycarbonate Urethane. A clamping element (5) (shown in FIGS. 2*a*-2*c*, 3*a*-3*c*, 5 and 6) presses the filling piece (3) against the connection element (2) in a non-positive fashion, which is also referred to herein as a force-fit or a frictional fashion. FIG. 1*b* shows how the filling piece (3) rotates as soon as the elastic connection element (2) is exposed to tensile force or extension. The filling piece (3) is arranged such that its edge opposite to the direction of force impinges upon the surface of the elastic connection element and generates a form-fit contribution that increases the anchoring force substantially.

Figure 2A:
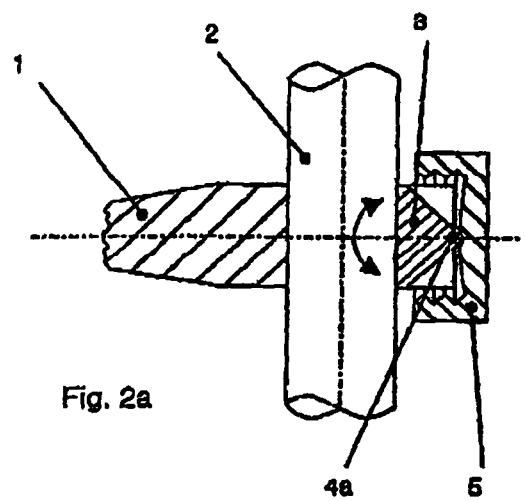
FIG. 2*a* shows a side view of a, for example, round connection element in a pedicle screw with a filling piece, a pivot point with spherical surface, and a clamping element.
Figure 2B:
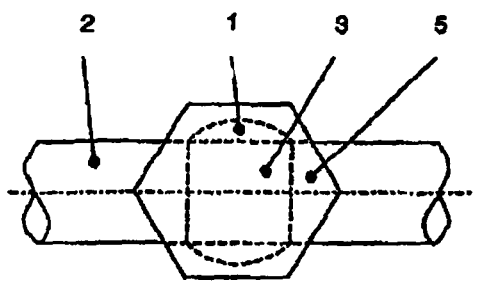
FIG. 2*b* shows a frontal view of the elements shown in FIG. 2*a*.
Figure 2C:
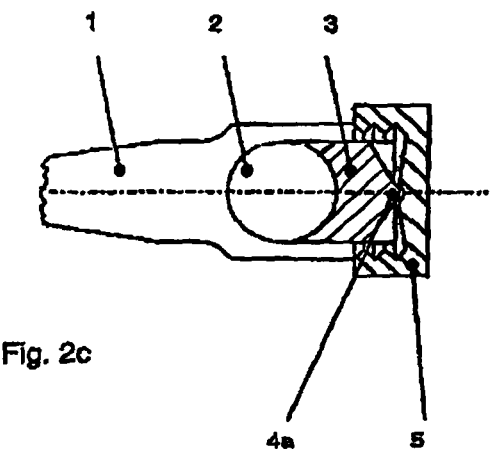
FIG. 2*c* shows a top view of the elements shown in FIG. 2*a*.

FIGS. 2*a*, 2*b*, and 2*c* show a side, frontal, and top view, respectively, of the elastic connection element (2), pedicle screw (1), filling piece (3), and clamping element (5). The clamping element (5) directly presses the rotatable filling piece (3) against the connection element (2) via a spherical surface (4a).

Figure 3A:
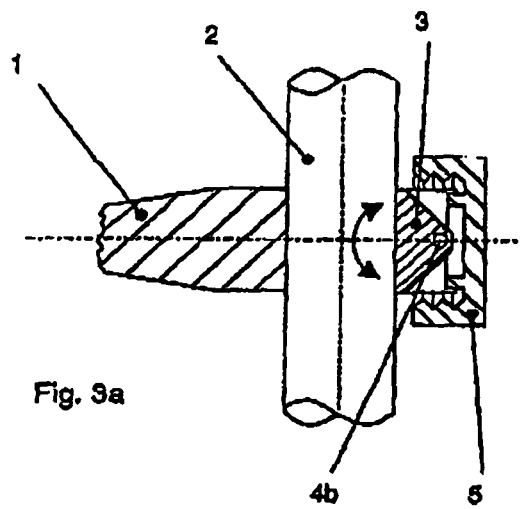
FIG. 3*a* shows a side view of a, for example, round connection element in a pedicle screw with a filling piece, a pivot point in an axis, and a clamping element.
Figure 3B:
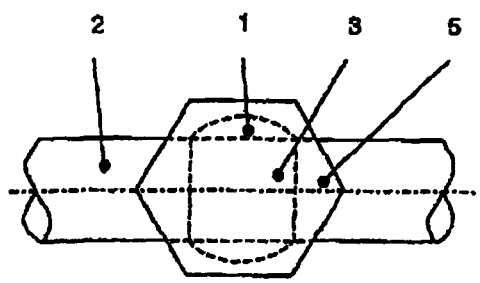
FIG. 3*b* shows a frontal view of the elements of FIG. 3*a*.
Figure 3C:
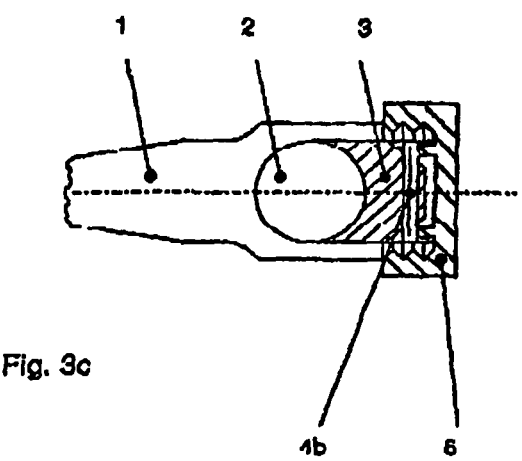
FIG. 3*c* shows a top view of the elements of FIG. 3*a*.

FIGS. 3a, 3b, and 3c show a side, frontal, and top view, respectively, of the elastic connection element (2), pedicle screw (1), filling piece (3), and clamping element (5). The clamping element (5) presses the rotatable filling piece (3) against the connection element (2) via a pin (4b).

Figure 4A:
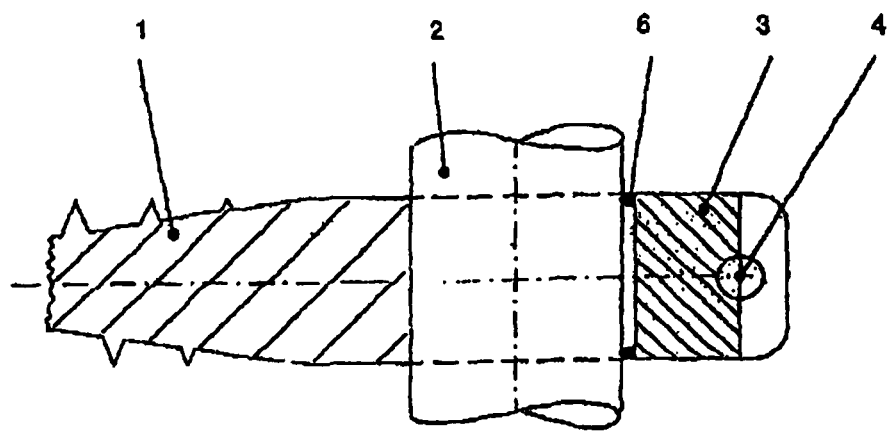
FIG. 4*a* shows an elastic connection element in a (sectioned) pedicle screw with a filling piece, which includes ribs, in neutral position about the pivot point.
Figure 4B:
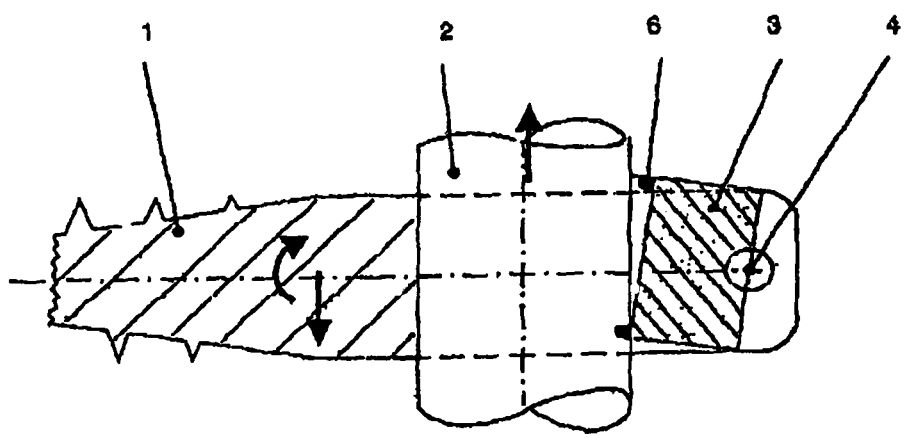
FIG. 4*b* shows an elastic connection element exposed to tensile force with the filling piece, which includes ribs, in rotated position about the pivot point.

FIG. 4a also shows an elastic connection element (2) in a pedicle screw (1) (shown in cross section) with a rotatable filling piece (3) in a neutral position about a pivot point (4). FIG. 4b shows how the filling piece (3) rotates as soon as the elastic connection element (2) is exposed to tensile force or extension. In this embodiment, the filling piece (3) comprises ribs (6), which slightly impinge upon the surface of the elastic connection element (2) even in the neutral position. Thus, the ribs (6) increase the initial resistance on the filling piece (3) which supports its rotation in the direction of force.

Figure 5:
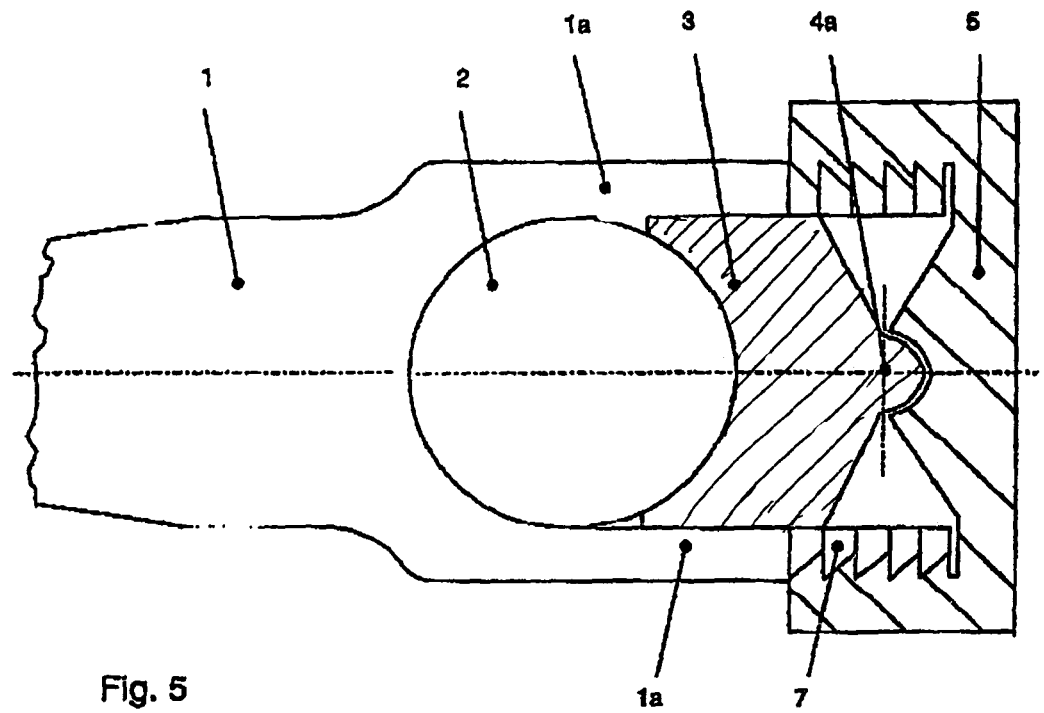
FIG. 5 shows a top view of a, for example, round connection element in a pedicle screw with screw wings, with a filling piece, a pivot point with spherical surface, and a clamping element connected to the screw via a saw tooth thread.

FIG. 5 shows a top view of, for example, a round connection element (2) in a pedicle screw (1) with a filling piece (3), a pivot point with spherical surface (4a), and a clamping element (5) that is connected to the screw via a saw tooth thread (7). The saw tooth thread prevents compression of the two screw wings (1a) to possibly restrict the mobility of the filling piece (3).

Figure 6:
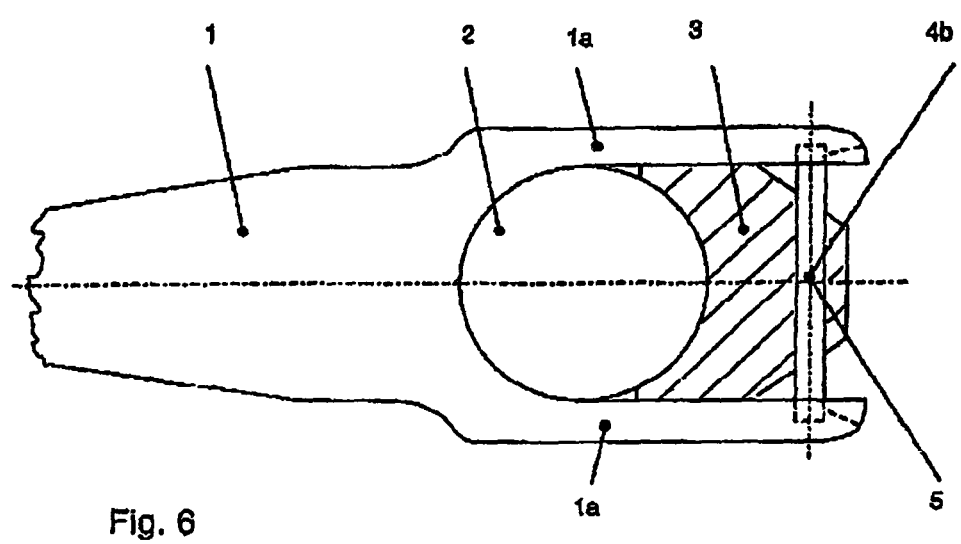
FIG. 6 shows a top view of a, for example, round connection element in a pedicle screw, with a filling piece, a pivot point in an axis and the same axis as clamping element.

FIG. 6 shows a top view of a, for example, round connection element (2) in a pedicle screw (1), with a filling piece (3), a pivot point in a pin (4b), whereby this pin simultaneously serves as clamping element (5) and is positioned by elastic spreading of the screw wings (1a).

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A spinal column implant comprising:
   an elastic connection element having a longitudinal axis;
   a plurality of bone screws, each bone screw comprising a screw head having a receptacle, a filling piece, a pin extending through the filling piece, and a clamping element, the receptacle having two legs defining a U-shaped recess;
   wherein the pin is located in the U-shaped recess;
   wherein the clamping element clamps the connection element into a clamped position between the receptacle of the screw head and the filling piece in a secure, non-positive fashion to transfer expected tensile and compressive forces between neighboring vertebrae for stabilizing the spinal column;
   wherein when the connection element is in the clamped position in the receptacle, the filling piece is pivotable relative to the clamping element about the pin and about an axis intersecting each leg in response to the expected tensile force being applied to the connection element, and
   wherein the pin defines a pivoting axis intersecting each leg.

2. A spinal column implant according to claim 1, wherein the pin is held by the clamping element.

3. A spinal column implant according to claim 1, wherein the connection element is a rod.

4. A spinal column implant according to claim 3, wherein the rod is round.

5. A spinal column implant according to claim 1, wherein the connection element comprises a plastic material.

6. A spinal column implant according to claim 5, wherein the connection element is made of Polycarbonate Urethane.

7. A spinal column implant according to claim 1, wherein the clamping element is a screw nut.

8. A spinal column implant according to claim 7, wherein the clamping element is connected to the screw head with a saw tooth thread.

9. A spinal column implant according to claim 1, wherein the pin simultaneously serves as the clamping element.

10. The spinal column implant of claim 1, wherein the pivoting of the filling piece deforms a portion of the connection element in response to the tensile force to enhance the clamping of the connection element with increase in the expected tensile force.

11. The spinal column implant of claim 1, wherein the pin is located between the two legs on a center of the axis intersecting each leg.

12. A spinal column implant comprising:
   an elastic connection element comprising a plastic material, the elastic connection element having a longitudinal axis; and
   a bone screw comprising:
      a screw head having a receptacle configured to receive the connection element, the receptacle having two legs defining a U-shaped recess;
      a filling piece mountable in the receptacle over the connection element, at least a portion of the filling piece configured to contact a portion of the connection element,
      a pin extending through the filling piece, the filling piece being pivotable in the receptacle about the pin and an axis intersecting each leg in response to expected tensile force being exerted on the connection element along the longitudinal axis of the connection element, wherein the pin is located in the U-shaped recess; and
      a clamping element configured to clamp the connection element into a clamped position in the receptacle in a secure, non-positive fashion to transfer the expected tensile force and an expected compressive force between neighboring vertebrae for stabilizing the spinal column;
   wherein pivoting of the filling piece about the pin relative to the clamping element in response to the expected tensile force when the connection element is in the clamped position in the receptacle deforms the portion of the connection element in contact with the portion of the filling piece in a positive fashion to enhance the clamping of the connection element with increase in the expected tensile force, and
   wherein the pin defines a pivoting axis intersecting each leg.

13. A spinal column implant according to claim 12, wherein the pin is held by the clamping element.

14. A spinal column implant according to claim 13, wherein the pin simultaneously serves as the clamping element.

15. A spinal column implant according to claim 12, wherein the connection element is a rod.

16. A spinal column implant according to claim 15, wherein the rod is round.

17. A spinal column implant according to claim 16, wherein the connection element is made of Polycarbonate Urethane.

18. A spinal column implant according to claim 12, wherein the clamping element is a screw nut.

19. A spinal column implant according to claim 18, wherein the clamping element is connected to the screw head with a saw tooth thread.

20. The spinal column implant of claim 12, wherein the deforming of the portion of the connection element in the positive fashion provides positive fit clamping in addition to the non-positive fit clamping via the clamping element.

21. A spinal column implant comprising:
an elastic connection element having a longitudinal axis;
a plurality of bone screws, each bone screw comprising a screw head having a receptacle with two legs defining a U-shaped recess for receiving the connection element, a filling piece, a pin extending through the filling piece, and a clamping element;
wherein the pin is located in the U-shaped recess;
wherein the clamping element clamps the connection element into a clamped position between the receptacle of the screw head and the filling piece in a secure, non-positive fashion to transfer expected tensile and compressive forces between neighboring vertebrae for stabilizing the spinal column;
wherein when the connection element is in the clamped position in the receptacle between the legs, the filling piece is pivotable about the pin relative to the clamping element and the legs in response to the expected tensile force being applied to the connection element, and
wherein the pin defines a pivoting axis intersecting each leg.

22. A spinal column implant comprising:
an elastic connection element having a longitudinal axis;
a bone screw comprising a screw head having a receptacle, a filling piece, a pin extending through the filling piece, and a clamping element, the receptacle having two legs defining a U-shaped recess;
wherein the pin is located in the U-shaped recess;
wherein the clamping element clamps the connection element into a clamped position between the receptacle of the screw head and the filling piece in a secure, non-positive fashion to transfer expected tensile and compressive forces between neighboring vertebrae for stabilizing the spinal column;
wherein when the connection element is in the clamped position in the receptacle between the legs, the filling piece is pivotable about the pin relative to the clamping element and the legs in response to the expected tensile force being applied to the connection element, and
wherein the pin defines a pivoting axis intersecting each leg.

23. A spinal column implant comprising:
an elastic connection element having a longitudinal axis;
a plurality of bone screws, each bone screw comprising a screw head having a receptacle, a filling piece, a pin extending through the filling piece, and a clamping element, the receptacle having two legs defining a U-shaped recess;
wherein the pin is located in the U-shaped recess;
wherein the clamping element clamps the connection element into a clamped position between the receptacle of the screw head and the filling piece in a secure, non-positive fashion to transfer expected tensile and compressive forces between neighboring vertebrae for stabilizing the spinal column;
wherein when the connection element is in the clamped position in the receptacle, the filling piece is pivotable relative to the clamping element about the pin and about an axis intersecting each leg in response to the expected tensile force being applied to the connection element, and
wherein the pin contacts the clamping element.

24. A spinal column implant comprising:
an elastic connection element comprising a plastic material, the elastic connection element having a longitudinal axis; and
a bone screw comprising:
a screw head having a receptacle configured to receive the connection element, the receptacle having two legs defining a U-shaped recess;
a filling piece mountable in the receptacle over the connection element, at least a portion of the filling piece configured to contact the connection element, the filling piece comprising a pivot defining a pivot axis extending through the two legs such that the filling piece is pivotable in the receptacle by a force component exerted on the connection element along the longitudinal axis of the connection element; and
a clamping element configured to clamp the connection element in the receptacle;
wherein the contact portion of the filling piece is below the pivot axis, the contact portion having a greater dimension in a direction of the longitudinal axis of the connection element than a dimension of the pivot in the direction of the longitudinal axis;
wherein pivoting of the filling piece deforms a portion of the connection element in contact with the contact portion of the filling piece to enhance the clamping of the connection element with increase in the force component, and
wherein the filling piece engages and is pivotable about a spherical surface of the clamping element.

25. A spinal column implant according to claim 24, wherein the filling piece engages and is pivotable about a pin.

26. A spinal column implant according to claim 24, wherein the filling piece comprises ribs configured to impinge upon a surface of the connection element.

* * * * *

UNITED STATES PATENT AND TRADEMARK OFFICE
CERTIFICATE OF CORRECTION

PATENT NO. : 8,870,925 B2  Page 1 of 1
APPLICATION NO. : 11/520286
DATED : October 28, 2014
INVENTOR(S) : Stefan Freudiger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 487 days.

Signed and Sealed this
Sixth Day of June, 2017

Michelle K. Lee
*Director of the United States Patent and Trademark Office*